United States Patent [19]

Matalon

[11] 4,396,430

[45] Aug. 2, 1983

[54] NOVEL FOUNDRY SAND BINDING COMPOSITIONS

[76] Inventor: Ralph Matalon, 432 Cherry Hill Blvd., Camden, N.J. 08034

[21] Appl. No.: 231,294

[22] Filed: Feb. 4, 1981

[51] Int. Cl.$^3$ .......................... B28B 7/34; C08L 5/00
[52] U.S. Cl. .............................. 106/38.5 R; 106/38.3; 106/162
[58] Field of Search ................. 106/38.5 R, 38.3, 162, 106/74

[56] References Cited

U.S. PATENT DOCUMENTS

| | | | |
|---|---|---|---|
| 2,829,060 | 4/1958 | Emblem | 106/38.35 |
| 2,883,723 | 4/1959 | Moore et al. | 106/38.3 |
| 2,926,098 | 2/1960 | Ilenda et al. | 106/38.35 |
| 2,977,650 | 4/1961 | Ilenda et al. | 22/194 |
| 3,032,426 | 5/1962 | Lee | 106/38.35 |
| 3,074,802 | 1/1963 | Alexander et al. | 106/38.3 |
| 3,094,422 | 6/1963 | Reinhold | 106/38.3 |
| 3,239,521 | 3/1966 | Weldes | 260/247.7 |
| 3,255,024 | 6/1966 | Alexander et al. | 106/38.3 |
| 3,345,194 | 10/1967 | Weldes | 106/287 |
| 4,194,918 | 3/1980 | George et al. | 106/38.5 |
| 4,226,277 | 10/1980 | Matalon | 164/12 |

FOREIGN PATENT DOCUMENTS 1309606  4/1970  United Kingdom .

OTHER PUBLICATIONS

Soluble Silicates In Industry by J. G. Vail, American Chemical Society, Chapter IV, "Reactions", p. 72.

*Primary Examiner*—Lorenzo B. Hayes
*Attorney, Agent, or Firm*—Brumbaugh, Graves, Donohue & Raymond

[57] ABSTRACT

This application discloses two novel binding compositions for making silicate bonded cores and molds. In one of the binding compositions disclosed ammonia or an amine such as an ethanol amine is added to a concentrated alkali metal silicate in the amount generally in excess of 1 or 2 percent, but not so much as to decrease the solids content of the sodium silicate to more than about 95% of its original concentration. The precipitation or gellation which normally occurs in such systems can be dispersed by intensive mixing.

The second novel composition is an adjuvant suitable for use in silicate bonded sands, which adjuvant is obtained by reacting a reducing sugar, an optional dicarboxylic acid or acid anhydride and boric acid. The dicarboxylic acid or acid anhydride comprises from 0% to 12% by weight of mixture, the boric acid comprises from $\frac{1}{2}$% to 2% of the mixture and the balance is the reducing sugar.

7 Claims, No Drawings

NOVEL FOUNDRY SAND BINDING COMPOSITIONS

This application relates generally to the manufacture of molds and cores for the casting of metals.

Metals such as light alloys, aluminum, bronze, gray irons and steels are frequently cast with the aid of casting forms such as cores and molds made of particles of a foundry sand bound together with a suitable binder. One type of binder which has been extensively used in the foundry industry is an aqueous solution of a soluble silicate such as sodium silicate, i.e., water glass.

Aqueous solutions of alkaline silicates are generally known to have adhesive properties, see, for example, Houwink et al. "Adhesion and Adhesives", Elsevier Publishing Co. 1965; Volume I, chapter 8; Vail, "Soluble Silicates", Rheinhold Publishing Co. 1952. Traditionally adhesion was developed by slow drying below the boiling point of water to avoid destruction of the adhesive film. (Vail supra, Vol. II, page 411). Because of the need for relatively slow drying, other means of rapid hardening the sodium silicate were required. To provide the rapid hardening required in practical foundry operation, it became known to use an acidic gas such as carbon dioxide or hydrochloric acid which rapidly converts the silicate into silica gel with a liberation of water and an alkaline carbonate. After an initial set has been obtained, the mold may then be baked to prepare it for use.

The carbon dioxide-hardened, silicate-bound foundry sand, however, has generally been recognized to lack adequate strength particularly under the conditions of high production volume such as encountered in the automotive industry. Accordingly, for the past twenty year foundry sand users have sought alternatives to the use of silicate as a binder for foundry sands. These alternatives have resided largely in the use of a variety of synthetic resins which are cured to provide the desired set to the mold.

An improved method of rapidly hardening foundry cores and molds is described in my U.S. Pat. No. 4,226,277. In accordance with the procedure described in that patent, silicate bonded foundry sands are hardened in a matter of two minutes or less by using forced drying conditions. This may be done by sucking or blowing large amounts of air through the sand core or mold held in a mold box having two or more air permeable faces. Alternatively, microwave heating or vacuum drying may be used. Typically, forced drying conditions in accordance with the method described in U.S. Pat. No. 4,226,277 are such that within a period not exceeding two minutes, at least 30 percent of the water originally present in the silicate binder is removed. In accordance with this procedure, the water content of this silicate binder should usually be dried sufficiently rapidly that the binder reaches solids content of 54% within two minutes, and preferably drying is sufficient to remove 50% to 75% of the water content of the binder within this time. For a more complete description of the forced drying method of hardening foundry core and molds, reference may be had by my U.S. Pat. No. 4,226,277 the disclosure of which is hereby incorporated by reference.

This application concerns improved silicate binders and adjuvants adapted for use in the forced drying method of my forementioned U.S. Pat. No. 4,226,277. Such binders and adjuvants, however, are also useful in other methods of core hardening, for example, carbon dioxide hardening or hardening upon standing in ambient air.

The simplest silicate binders are exemplified by water glass, i.e., sodium silicate containing silica, sodium oxide and water in varying proportions. It is, of course, well known that there are a variety of alkali metal silicates, and all of these may be used in substitution for sodium silicate. Such other common alkali metal silicates are potassium silicate and lithium silicate. Also quaternary ammonium silicate can be used in combination with the alkali metal silicates. Such quaternary ammonium silicates are described, for example in U.S. Pat. Nos. 3,239,521, 3,345,194 and 3,372,038.

Silicate binders generally have silica to metal oxide mole ratios of 1:1 to 4:1, and preferably from 2.2:1 to 3.2:1. These proportions correspond generally to metasilicates, disilicates, trisilicates or higher silicates. Such silicates in solution are characterized by increasing amounts of branched rings and complex structures characterized as "polysilicate anions", and it is believed that it is the branched ring and complex structure which give rise to the binding properties of aqueous silicates.

The silicate binder also contains water to form a syrup-like aqueous composition having colloidal or gel-like film-forming characteristics. In commercially practicable silicates, there is generally from 47% to 70% water, the soluble silicate solution having a viscosity ranging from 100 cp up to 50,000 cp–70,000 cp depending upon the amount of water and the composition of the silicate. I have had best results in using, as the soluble silicates, sodium silicate "N", sodium silicate "K", sodium silicate "RU" and sodium silicate "D" of the Philadelphia Quartz Company. The grade "N" soluble silicate contains silica to sodium oxide in a 3.22 weight ratio, the syrup containing 37.2% sodium silicate solids, having a density of 41.0° Be and a viscosity of 180 cp. Grade "K" has a $SiO_2:Na_2O$ ratio of 2.88 and contains 42.7% solids. Grade "RU" has a silicate to sodium oxide weight ratio of 2.40, a solids content of 47%, a density of 52.0° Be and a viscosity of 2100 cp. Grade "D" has a $SiO_2:Na_2O$ ratio of 2.0 contains 44.1% solids.

Sodium oxide when present in a soluble silicate binder tends to reduce the melting point of the foundry sand. This imparts adverse shake-out properties, and is more severe with the more alkaline water glasses, notwithstanding that the more alkaline silicates produce better tensile properties in the mold. At the same time, however, while a soluble silicate containing a high ratio of silicate to soda such as 3.6, for example, affords favorable shake-out characteristics, it tends to produce relatively weak binding. Accordingly, there is a desire, notwithstanding the adverse effect of soda, to use a soluble silicate of the highest practical alkalinity-lowest practical ratio of silicate to soda.

In part, this difficulty can be mitigated by replacing some of the sodium oxide of water glass by other alkali metal oxides such as potassium. Such other alkali metals have a lesser tendency than does sodium to flux the foundry sand and lower its fusion point, but they add to the expense of the binder.

In accordance with one aspect of the present invention, improved formulation for preparing silicate foundry binding core and molds can be prepared by substituting ammonia, or a primary, secondary or tertiary amine, or an alkaline quaternary ammonium compound (i.e., quaternary ammonium hydroxides) to the sodium silicate for the purpose of increasing its alkalinity without introduction of adverse quantities of sodium oxide.

In this aspect of the invention I use a concentrated sodium silicate containing at least 37% sodium silicate solids and having a silica to sodium ratio between 2.2 and 3.2 to which concentrated ammonia, an alkyl amine, or alkanol amine or a quaternary ammonium compound is added up to an amount (typically 1% to 2% or more based on the weight of the silicate) which increases the effective alkalinity of the sodium silicate. The amount of water added with the ammonia or amine should be limited, so that the solids content of the resulting mixture is not less than 95% of the solids content of the original solution. This aspect of the invention is particularly surprising because it had been thought heretofore that addition of ammonia to concentrated sodium silicate solutions tended to convert the sodium silicate to an insoluble gel. I have found the conditions (described below) which avoid this problem.

While in the foregoing reference has been made particularly to ammonia it will be understood that a variety of ammonia substitutes may also be used. Primary, secondary and tertiary lower alkyl or lower alkanol amines for example are also suitable, as are the quaternary ammonium hydroxides. Representative amines include mono-, di- and tri-methanol amines; and mono-, di- and tri-ethanol amines. The ethanol amines are preferred since both ammonia and the alkyl amines have objectionable odors. Objectionable odors are not as serious when ethanol amines are used in accordance with this aspect of the present invention.

As indicated, addition of amines to the alkali metal silicate solutions characteristically tends to cause gel formation. In accordance with the present invention, such gels can be dispersed by vigorous mixing for 10-30 minutes. It will be immediately apparent in the practice of this invention when the mixing has been sufficient since the gel formed by the addition of ammonia or the amine will result in discrete lumps of gel. When mixing has been sufficient, these will be broken up and dispersed. The dispersed gel may be allowed to age for several hours (or preferably a day or more) at room temperature. Typically, the dispersed gel after mixing will be substantially uniform and have a viscosity which is not more than twice the viscosity of the original sodium silicate. Under the preferred conditions the ammoniated silicate will actually be more fluid than the original sodium silicate used as a starting material.

The ammoniated silicate provides a binder with exceptional tensile properties. Moreover, because the ammonia (or the amine) is volatile under the influence of sand drying and the heat of casting, the ammonia (or amine) evaporates leaving behind a mold of excellent shake-out properties. Because the introduction of soda is limited, the foundry sand retains its reuseability for a greater period of time.

Another aspect of the present invention concerns adjuvants which may be used for reducing the tendency of the silicate binder to form glass-like substances during casting and improve the shake-out characteristics.

In general such adjuvants, under the influence of heat during casting, will decompose in a manner that disrupts the strength of the film or binding action of the silicate. For example, additives may carbonize upon exposure to temperatures of the casting metal, or may evolve small amounts of gases at such temperatures. This facilitates shake-out of the mold and cores from the finished casting. Preferred adjuvants are film-forming materials which will also enhance the strength properties of the silicate binder, so that the same or even improved strength is obtained with reduced amount of silicate.

The additives are preferably miscible with the silicate binder or dispersible therein, and have no detrimental effect on it. It has been found that a small amount of gas formed in the sand of the mold and core contributes to good casting. However, excessively gassy adjuvants should be avoided since large amounts of gas will cause porous castings, and adversely affect the cast surfaces and dimensional integrity of the casting. Additives rich in nitrogen, for example, are not preferred for this reason.

Preferred adjuvants which have been specially formulated for use with foundry sands bonded by a soluble silicate are formed from (i) a reducing sugar such as glucose, corn syrup or other reducing sugar such as fructose, lactose, mannose or levulose, (ii) a lower dibasic carboxylic acid or acid anhydride such as maleic acid, maleic anhydride, succinic acid, succinic anhydride, tartaric acid or anhydride, citric acid, etc. I have discovered that such binders can be improved by the addition of boric acid, which acts as a stabilizer to prevent the caramelization of the sugar. In accordance with this aspect of the invention, the boric acid may be used either in addition to or as a replacement for the dibasic carboxylic acid, although preferably both are used.

In general, the lower dibasic carboxylic acid should contain from 3 to 6 carbon atoms, be miscible with the reducing sugar at the processing temperature, and may contain hydroxy groups. Optionally there may also be included polyhydric alcohols containing 2 to 8 carbon atoms and 2 to 6 hydroxy groups, which alcohols function as plasticizers. Typical such alcohols are ethylene glycol, propylene glycol, glycerine, pentaerithritol and sorbitol.

The foregoing ingredients are blended together to form a mixture containing (on a dry weight basis) from 0 to 12% dibasic carboxylic acid anhydride and preferably from 1 to 3%; from ½ to 2% boric acid and preferably from ½ to 1%; and from 0 to 6% polyhydric alcohol, preferably from 0 to 4%. The balance of the composition is made up of the reducing sugar. The reducing sugar may be provided either as a dry powder or as an aqueous syrup containing up to 20% water. The proportions given above are based on the weight of the dry ingredients.

The mixture is heated to remove water contained in the reducing sugar. At the same time some water of condensation may also be removed since the amount of water evolved generally exceeds the amount of water introduced with the sugar. Heating generally is for a period of 30 to 90 minutes at a temperature of 110° C. to 150° C. The heating step should be continued until the mixture, upon cooling, forms a clear, glassy, non-crystallizing solid. However, heating should not be continued so long as to cause caramelization or thermal degradation of the adjuvant or to convert it into a solid so hard that it cannot be subsequently diluted with caustic. After heating to remove water, usually while the reaction mixture is still hot, an aqueous alkali is then added, such as an alkali metal hydroxide (NaOH, KOH, etc.) or ammonia. The amount of alkali and water added at this stage should be sufficient to provide from 10% to 25% water in the final product, and from about ½% to 2% alkali. The amount of alkali added should be sufficient to neutralize unreacted carboxylic acids and to aid in the dilution process. After cooling, the finished product is a syrupy fluid.

The present invention is illustrated by the following examples:

EXAMPLE 1

One and one half kilograms of New Jersey silica 50 (New Jersey Silica Company, average particle size 50) was combined with 24.2 gms. of a soluble silicate prepared by evaporating 12 gms. of water from 200 gms. of Type RU soluble silicate (Philadelphia Quartz Company) and adding 2 gms. sodium hydroxide thereto. In addition, 17.6 gms. of adjuvant P-13 were blended into the green sand.

P-13 adjuvant was prepared by combining 400 gms. of glucose (9% water), 6.6 gms. of maleic anhydride and 2.66 gms. of boric acid, the mixture was heated to 122° C.–133° C. for one hour during which 22.6 gms. of water was lost. While still hot, 40 cc of 10% sodium hydroxide and 34 cc of water were added. The mixture, when cooled to room temperature, was tacky and capable of drying in air.

The green sand was packed into a mold for tensile bar samples and hardened by drawing air through it at 220° F. and at a rate of about 100 cfm with an aid of a vacuum blower. The tensile bar mold was provided with two air-permeable faces in accordance with the apparatus for making such bars disclosed in my above-mentioned U.S. Pat. No. 4,226,277. After forced drying for periods of 10 to 45 seconds, the following results were obtained:

| Drying Time | Instantaneous Tensile Strength | Water Loss |
| --- | --- | --- |
| 10 seconds | 24 psi | 0.4 gms. |
| 15 seconds | 40 psi | 0.55 gms. |
| 20 seconds | 46 psi | 0.57 gms. |
| 30 seconds | 58 psi | 0.64 gms. |
| 45 seconds | 104 psi | 0.86 gms. |

EXAMPLE 2

An adjuvant containing boric acid as was prepared by combining 300 grams of glucose, 5 grams of maleic acid and 2 grams of boric acid. The mixture was heated for approximately 35 minutes during which time the temperature rose from 120° C. to 134° C. and 19 grams of water were lost. While still hot 30 cc of 10% sodium hydroxide 26 cc of water were added. Thereafter, the mixture was cooled.

The adjuvant thus prepared was combined with sodium silicate type RU in varying proportions and employed to form test bars employing New Jersey silicate sand No. 65. The sand was then hardened by allowing it to stand in ambient air for 24 hours. The following results were obtained:

| Parts of Sodium Silicate Per 100 Parts of Sand | Amount of Adjuvant Per 100 Parts of Sand | Tensile Strength |
| --- | --- | --- |
| 3 | 2 | 160 psi |
| 2.5 | 2.5 | 160 psi |
| 1.7 | 3.3 | 224 psi |
| 1.25 | 3.75 | 208 psi |
| 2.2 | 0.85 | 128 psi |
| 1 | 2 | 184 psi |
| 3 | 0 | 40 psi |

EXAMPLE 3

An adjuvant was prepared by combining 400 grams of glucose, 2.66 grams of citric acid and 2.66 grams of boric acid. The mixture was heated for about 35 minutes during which time the temperature rose 122° C. to 135° C. and 22.6 grams of water was evolved.

Thereupon, 40 cc of 10% sodium hydroxide and 34 cc of water were added. After the mixture had cooled to room temperature, it was combined with varying amounts of sodium silicate type RU, and the mixture employed as a binding agent to prepare standard tensile test bars. Some of the tensile bars were hardened by allowing them to stand in ambient air for 24 hours. Other samples of the same mixtures were hardened using carbon dioxide. The following results were obtained:

| Parts of Sodium Per-Parts of Sand | Amount of Adjuvant Per-Parts of Sand | Tensile Strength Air Hardened | Tensile Strength $CO_2$ Hardened |
| --- | --- | --- | --- |
| 3.6 | 0 | 140 | 72 |
| 0 | 3.6 | 88 | — |
| 1.8 | 1.8 | — | 112 |
| 1.2 | 2.4 | 100 | 80 |

EXAMPLE 4

An ammoniated silicate for use in accordance with the present invention was prepared as follows:

38 grams of Type N soluble silicate (silica to sodium oxide ratio 2.33, 37% solids) were combined with 3.8 grams of concentrated ammonium hydroxide (28% ammonia). The mixture was shaken intensely for a minute or two. At this point a slight gel appeared. The mixture was then allowed to set overnight. The following day the gel had disappeared and a homogeneous solution resulted which was more fluid than the original Type N soluble silicate.

EXAMPLE 5

41 grams of a sodium-ammonium silicate prepared as in Example 4 were combined with 1 kg. Portage sand of average particle size 60. The mixture was packed into standard tensile test molds and hardened in 220° F. air as described in Example 1. The following results were obtained:

| Drying Time | Instantaneous Tensile Strength psi | Water Loss Grams | Water Loss Percent |
| --- | --- | --- | --- |
| 20 seconds | 24 | 0.89 | 34.4 |
| 30 seconds | 60 | 1.30 | 50.3 |
| 45 seconds | 93 | 1.69 | 65.6 |
| 55 seconds | 125 | 1.97 | 76. |
| 65 seconds | 190 | 2.12 | 82.1 |
| 75 seconds | 168 | 2.23 | 86.4 |

For comparison purposes, a similar sample was made using Type N soluble silicate as a binder without any ammonia having been added thereto. When these samples were tested for strength, the following results were obtained:

| Drying Time | Instantaneous Tensile Strength psi |
|---|---|
| 20 seconds | 18 |
| 30 seconds | 40 |
| 45 seconds | 64 |
| 55 seconds | 88 |
| 65 seconds | 88 |
| 75 seconds | 116 |

EXAMPLE 6

Following generally the procedures of Examples 4 and 5, an ammoniated silicate was prepared from Type RU soluble silicate to which ammonia has been added to provide an ammoniated silicate containing 2% ammonia. 20 grams of the ammoniated sodium silicate were combined with 1 kg. of Portage sand. The mixture was packed into standard tensile test molds and dried in 220° F. air as described in Example 1. For comparison purposes, corresponding samples were made from mixture of 1 kilogram of Portage sand with 22 grams of Type RU soluble silicate. The following results were obtained:

| | Instantaneous Tensile Strength psi | |
|---|---|---|
| Drying Time | Type RU plus 2% Ammonia | Type RU |
| 10 seconds | 26 | 18 |
| 15 seconds | 52 | 32 |
| 20 seconds | 80 | 48 |
| 25 seconds | 98 | 62 |
| 30 seconds | 98 | 84 |
| 45 seconds | 160 | 84 |

EXAMPLE 7

A series of ammoniated sodium silicates were prepared by adding ammonium hydroxide (28%) to various sodium silicate solutions. Immediately following addition of the ammonium hydroxide, the mixture was vigorously stirred by hand for 30 to 40 minutes. The resulting solutions were homogeneous. They were then allowed to age at least 3 to 4 hours (in some samples aging was overnight). The amount added was sufficient in each sample to increase the alkalinity to the equivalent of a 2.1 ratio silicate. In each case the viscosity of the ammoniated sodium silicate was less than the viscosity of the original sodium silicate.

Tensile test bars were then prepared using sand containing about 1½% silicate binder (dry solid basis). For comparison purposes, a similar series of samples were prepared from the sodium silicates employed in these tests before ammonia had been added. The following results were obtained:

| | | | Tensile Strength | |
|---|---|---|---|---|
| Sodium Silicate Type | Soda/Silica Ratio | Sample Drying Time | Initial Sodium Silicate | Ammoniated Sodium Silicate |
| Type RU | 2.4 | 45 sec. | 84 | 160 |
| Type K | 2.88 | 120 sec. | 110 | 178 |
| Type N | 3.2 | 45 sec. | 64 | 93 |
| Type S-35 | 3.75 | 90 sec. | 22 | 28 |

I claim:
1. A composition of matter for use in binding a particulate composition prepared by:
   (a) combining (i) a reducing sugar, (ii) an optional lower dibasic carboxylic acid or acid anhydride and (iii) boric acid, said dibasic carboxylic acid or acid anhydride being, on a dry weight basis, from 0 to 12% by weight of said mixture, and said boric acid being, on a dry weight basis, from ½ to 2% by weight of said mixture, the balance of said mixture being said reducing sugar.
   (b) heating said mixture to remove at least the water introduced with the sugar;
   (c) thereafter adding alkali and water to provide a final composition containing from 10 to 25% water and from about ½ to 2% alkali.

2. A composition according to claim 1 wherein there is at least 1% by weight of said dibasic carboxylic acid or acid anhydride.

3. A composition according to claim 2 wherein the amount of said dibasic carboxylic acid or acid anhydride is between 1% and 3%.

4. A composition according to claim 1, 2 or 3 wherein the amount or boric acid is between ½ and 1%.

5. The composition according to claim 1, 2 or 3 which additionally contains from 0 to 6% of a polyhydric alcohol.

6. A composition according to claim 5 wherein the amount of polyhydric alcohol is not more that 4%.

7. The composition according to claim 1, 2 or 3 wherein said alkali is an alkali metal or ammonium hydroxide.

* * * * *

UNITED STATES PATENT AND TRADEMARK OFFICE
CERTIFICATE OF CORRECTION

PATENT NO. : 4,396,430
DATED : August 2, 1983
INVENTOR(S) : Ralph Matalon

It is certified that error appears in the above—identified patent and that said Letters Patent is hereby corrected as shown below:

Col. 3, line 27, "tri-methanol" should be --tri-methyl--;

Col. 3, line 27, after "amines;" insert --mono-, di- and tri-ethyl amines;--

Col. 8, line 42, "or" should be --of--.

Signed and Sealed this

Thirteenth Day of December 1983

[SEAL]

Attest:

GERALD J. MOSSINGHOFF

Attesting Officer

Commissioner of Patents and Trademarks